US008916543B1

(12) United States Patent (10) Patent No.: US 8,916,543 B1
O'Callaghan et al. (45) Date of Patent: Dec. 23, 2014

(54) INHIBITORS OF ALPHA-TOXIN

(75) Inventors: Richard J. O'Callaghan, Ridgeland, MS (US); Clare C. McCormick, Jackson, MS (US); Armando R. Caballero, Jackson, MS (US); Charles L. Balzli, Brandon, MS (US); Aihua Tang, Jackson, MS (US)

(73) Assignee: University of Mississippi Medical Center, Jackson, MS (US)

( * ) Notice: Subject to any disclaimer, the term of this patent is extended or adjusted under 35 U.S.C. 154(b) by 268 days.

(21) Appl. No.: 12/773,556

(22) Filed: May 4, 2010

Related U.S. Application Data

(60) Provisional application No. 61/175,385, filed on May 4, 2009.

(51) Int. Cl.
| | | |
|---|---|---|
| *A61K 31/716* | (2006.01) | |
| *A61K 31/575* | (2006.01) | |
| *A61K 31/724* | (2006.01) | |

(52) U.S. Cl.
CPC ............ *A61K 31/724* (2013.01); *A61K 31/575* (2013.01)
USPC .......................................................... 514/58

(58) Field of Classification Search
CPC A61K 31/724; A61K 31/575; A61K 2300/00
See application file for complete search history.

(56) References Cited

U.S. PATENT DOCUMENTS

| | | | |
|---|---|---|---|
| 4,804,539 | A | 2/1989 | Guo et al. |
| 6,791,059 | B2 | 9/2004 | Smart |
| 6,878,899 | B2 | 4/2005 | Smart |
| 7,906,498 | B2 | 3/2011 | Marquart et al. |
| 2004/0224010 | A1 | 11/2004 | Hofland et al. |

OTHER PUBLICATIONS

Kattan HM, et al., Nosocomial Endophthalmitis Survey. Current Incidence of Infection after Intraocular Surgery. Ophthalmology. 1991;98(2):227-238.
Kielian T, et al., Diminished Virulence of an Alpha-Toxin Mutant of *Staphylococcus aureus* in Experimental Brain Abscesses. Inject Immun. 2001;69(11):6902-6911.
Klevens RM, et al., Changes in the Epidemiology of Methicillin-Resistant *Staphylococcus aureus* in Intensive Care Units in US Hospitals, 1992-2003. Clin Infect Dis. 2006; 42(3):389-391.
Liang X, Ji Y. Involvement of α5β1-integrin and TNF-α in *Staphylococcus aureus* α-toxin-induced death of epithelial cells. Cell Microhiol. 2007;9(7)1809-1821.

Marquart ME et al., Cholesterol as Treatment for Pneumococcus Keratitis: Cholesterol-Specific Inhibition of Pneumolysin in the Cornea, Invest Ophthalmol Vis Sci., 2007, 48(6): 2661-2666.
McCormick C et al., Diverse Virulence of *Staphylococcus aureus* Strains for the Conjunctiva, Current Eye Search, 36(1), 2011, pp. 14-20.
McCormick C et al., Fluoroquinolone Prophylaxis for Experimental MRSA Keratitis in a LASIK Model, 2007, OMIG. (Abstract only).
McCormick C et al., The Bactericidal Effectiveness of an Enhanced Tobramycin-Dexamethasone Formulation, Invest Ophthalmol Vis. Sci., 2008, vol. 49. (Abstract only).
McCormick CC et al., Chemical Inhibition of Alpha-Toxin, a Key Corneal Virulence Factor of *Staphylococcus aureus*; Investigative Ophthalmology & Visual Science, 2009, vol. 50, (6), pp. 2848-2854.
McCormick CC et al., The Effectiveness of Lysostaphin Therapy for Experimental Coagulase-Negative *Staphylococcus* Endophthalmitis, Current Eye Research, 31, 2006, pp. 225-230.
Monds KS et al., Alpha-Toxin Susceptibility Impacts Age-Related Differences in Experimental *S. aureus* Keratitis, Invest Ophthalmol Vis. Sci., 2006, vol. 47. (Abstract only).
Moran GJ, et al., Methicillin-Resistant *S. aureus* Infections among Patients in the Emergency Department. N Engl J Med. 2006;355(7):666-674.
Moreau JM et al., Effectiveness of ciprofloxacin-polystyrene sulfonate (PSS), ciprofloxacin and ofloxacin in a *Staphylococcus* keratitis model, Current Eye Research, pp. 808-812, 1998.
Moreau JM et al., *Staphylococcus* Model of Keratitis Used to Compare the Effectiveness of Three Fluoroquinolones, 4072. (Abstract only), 1997.
Moreau JM, et al., Phospholipase A2 in Rabbit Tears: A Host Defense against *Staphylococcus aureus*, Investigative Ophthalmology & Visual Science, Sep. 2001, vol. 42, (10), pp. 2347-2354.
Moreau JM, et al., Histopathological studies of staphylococcal alpha-toxin: effects on rabbit corneas. Curr Eye Res. 1997;16(12):1221-1228.
O'Callaghan RJ et al., Bacterial Products Responsible for Tissue Damage During Bacterial Keratitis, 1136. (Abstract only), 1997.
O'Callaghan RJ et al., Effectiveness of Moxifloxacin and Quixin™ in a Rabbit Model of *Staphylococcus* Keratitis, 2001, OMIG. (Abstract only).
O'Callaghan RJ et al., *Pseudomonas* Versus *Staphylococcus*: Topical Inoculation of the Rabbit Cornea, 806. (Abstract only), 2000.
O'Callaghan RJ et al., Specific Roles of Alpha-Toxin and Beta-Toxin during *Staphylococcus aureus* Corneal Infection, Infection and Immunity, 1997, vol. 65, No. 5, pp. 1571-1578.
Yotis WW, et al., Reduction of the cytolytic action of staphylococcal alpha-toxin by progesterone. Yale J Biol Med. 1970;42(6):411-419.

(Continued)

*Primary Examiner* — Layla Bland
*Assistant Examiner* — Bahar Craigo
(74) *Attorney, Agent, or Firm* — Stites & Harbison PLLC; Richard S. Myers, Jr.

(57) ABSTRACT

Aspects of the present invention include methods for inhibiting damage to a mammalian cornea, comprising administering an effective α-toxin inhibiting about of a composition that comprises a β-cyclodextrin and cholesterol.

6 Claims, 3 Drawing Sheets

(56) References Cited

OTHER PUBLICATIONS

O'Callaghan RJ et al., The Rabbit Intrastromal Injection Model of Bacterial Keratitis, Handbook of Animal Models of Infection, O Zak and M Sande (eds), Academic Press, London, 1999, pp. 367-374.
O'Callaghan RJ, et al., Host defense against bacterial keratitis, Ocular Immunology and Inflammation, 2003, vol. 11, No. 3, pp. 171-181.
O'Callaghan, RJ et al., Age-Related Differences in Rabbits During Experimental *Staphylococcus aureus* Keratitis, Investigative Ophthalmology & Visual Science, Nov. 2007, vol. 48, No. 11, pp. 5125-5131.
O'Callaghan RJ. Role of Exoproteins in Bacterial Keratitis: The Fourth Annual Thygeson Lecture, Presented at the Ocular Microbiology and Immunology Group Meeting, Nov. 7, 1998. Cornea. 1999;18(5):532-537.
Pany S, et al., Caveolin-1 binding motif of α-hemolysin: its role in stability and pore formation. Biochem Biophys Res Commun. 2004;322(1)29-36.
Phillips Jr, et al., Staphylococcal α-Toxin Causes Increased Tracheal Epithelial Permeability. Pediatr Pulmonol. 2006; 41(12):1146-1152.
Raff MJ, et al., Detoxification of staphylococcal α-toxin by hydrocortisone and methylprednisolone. J Med Microbiol. 1977; 11(1):67-73.
Reed JM et al., Ocular Virulence of Capsule-Deficient *Streptococcus pneumoniae* in a Rabbit Keratitis Model, Invest Opht Vis Sci, 2005, 46.
Sloop GD et al., Acute Inflammation of the Eyelid and Cornea in *Staphylococcus* Keratitis in the Rabbit, Investigative Ophthalmology & Visual Science, Feb. 1999, vol. 40, No. 2. pp. 385-391.
Stroman DW et al., Combination of Pharamacokinetics and Susceptibility Data as Predictive Indicator of Bacterial Keratitis, 2004, OMIG. (Abstract only).
Tang A et al., A New Topical Model of *Staphylococcus aureus* Keratitis in a Scarified Rabbit Eye, Investigative Ophthalmology & Visual Science, 2009, vol. 50, 2397. (Abstract only).
Valeva A, et al. Molecular architecture of a toxin pore: a 15-residue sequence lines the transmembrane channel of staphylococcal α-toxin. EMBO J 1996; 15(8): 1857-1864.
Vijayvargia R, et al. Assembly of α-hemolysin on A431 cells leads to clustering of Caveolin-1. Biochem Biophys Res Commun. 2004;324(3):1124-1129.
Vijayvargia R, et al., Functional form of Caveolin-1 is necessary for the assembly of α-hemolysin. Biochem Biophys Res Commun. 2004;324(3):1130-1136.
Alionte LG et al., *Pseudomonas aeruginosa* LasA protease and corneal infections, Current Eye Research (2001) vol. 22, 4, pp. 266-271.
Balzli CL, et al. Fluoroquinolone therapy in a rabbit model of post-LASIK methicillin-resistant *Staphylococcus aureus* keratitis, Laboratory Science, J Cataract Refract Surg (2008) 34, 295-301.
Balzli CL, et al., A High Virulent *Staphylococcus aureus*: Rabbit Anterior Chamber Infection, Characterization, and Genetic Analysis, Invest. Ophthalmol Vis. Sci., 2010, vol. 51, No. 10, 5114-5120.
Balzli CL, et al., Penetration and effectiveness of prophylactic fluoroquinolones in experimental methicillin-sensitive or methicillin-resistant *Staphylococcus aureus* anterior chamber infections, J Cataract Refract Surg (2010), 36, 2160-2167.
Balzli CL, et al., Prophylactic Treatment of *Staphylococcus aureus* Infection in the Rabbit Anterior Chamber with Vigamox or Besivance, 2009. (Abstract only).
Balzli CL, et al., Sustained Anit-Staphylococcal Effect of Lysostaphin in the Rabbit Aqueous Humor, Current Eye Research (2010), 35(6), 480-486.
Bergsma DR, et al., Quantification of the Immune Response During Bacterial Keratitis, p. 3647. (Abstract only) 1992.
Caballero AR, et al., Effectiveness of Fluoroquinolones Against *Mycobacterium abscessus* In Vivo, Current Eye Research, 2006, 31:23-29.
Caballero AR, et al., Passive Immunization Therapy for Experimental Staphylococcal Keratitis 2004, OMIG. (Abstract only).

Caballero AR., et al., A Newly Discovered Toxicity of *Staphylococcus aureus* Active in Experimental Keratitis, Invest Opht Vis Sci (2006) 47, 1914. (Abstract only).
Caballero AR., et al., Fluoroquinolone Therapy for Experimental LASIK-Associated *Staphylococcus* Keratitis, Invest Opht Vis Sci (2007) 48, 2675. (Abstract only).
Caballero AR., et al., Genetic Analysis of a New *Staphylococcus aureus* Isolate that Exhibits Exquisite Virulence in the Rabbit Cornea, Conjunctiva and Anterior Chamber, Invest Opht Vis Sci (2009) 50, 5112. (Abstract only).
Caballero AR., et al., Isolation and Characterization of a New *Staphylococcus aureus* Protease, Invest Opht Vis Sci (2008) 49, 5514. (Abstract only).
Caballero AR., et al., Ocular Pathology of a *Staphylococcus aureus* Mutant Lacking a Recently Discovered Virulence Factor, Invest Opht Vis Sci (2010) 51, 3891. (Abstract only).
Caballero AR., et al., Virulence of *Staphylococcus* epidermidis Strains in the Rabbit Cornea, Invest Opht Vis Sci (2005) 46, 2626. (Abstract only).
Callegan MC et al., Topical Antibiotic Therapy for the Treatment of Experimental *Staphylococcus aureus* Keratitis, Investigative Ophthalmology & Visual Science, vol. 33, No. 11, Oct. 1992, pp. 3017-3023.
Callegan MC, et al., Corneal Virulence of *Staphylococcus aureus*: Roles of Alpha-Toxin and Protein A in Pathogenesis, Infection and Immunity, Jun. 1994, Vo. 62, No. 6, pp. 2478-2482.
Callegan MC, et al., Efficacy of tobramycin drops applied to collagen shields for experimental staphylococcal keratitis, Current Eye Research, 1994, 875-878.
Callegan MC, et al., Methicillin-resistant *Staphylococcus aureus* keratitis in the rabbit: therapy with ciprofloxacin, vancomycin and cefazolin, Current Eye Research, vol. 11, No. 11, 1992, pp. 1111-1119.
Callegan MC, et al., Topical Antibiotic Therapy for the Treatment of Experimental *Staphylococcus aureus* Keratitis, Investigative Ophthalmology & Visual Science, vol. 33, No. 11, 1992, 3017-3023.
Callegan MC., et al., Efficacy of Topical Gylcopeptides for Multidrug-Resistant *S. aureus* Keratitis, 4729. (Abstract only), 1995.
Callegan, MC et al., Ciprofloxacin Versus Tobramycin for the Treatment of Staphylococcal Keratitis, Investigative Ophthalmology & Visual Science, Mar. 1994, vol. 35, No. 3, pp. 1033-1037.
Callegan, MC et al., Ocular drug delivery: a comparison of transcorneal iontophoresis to corneal collagen shields, International Journal of Pharmaceutics, 123, 1995, pp. 173-179.
Callegan, MC et al., Pharmacokinetic Considerations in the Treatment of Bacterial Keratitis, Pharmacokinetics-Therapeutics, Clin, Pharmacokinet, 1994, 27 (2), pp. 129-149.
Clinch TE et al., Collagen Shields Containing Tobramycin for Sustained Therapy (24 Hours) of Experimental *Pseudomonas* Keratitis, The CLAO Journal, Oct. 1992, vol. 18, No. 4, pp. 245-247.
Dajcs JJ et al., Lysostaphin is effective in treating methicillin-resistant *Staphylococcus aureus* endophthalmitis in the rabbit, Current Eye Research, 2001, vol. 22, No. 6, pp. 451-457.
Dajcs JJ, et al., Corneal Pathogenesis of *Staphylococcus aureus* Strain Newman, Invest Ophthalmol Vis. Sci, 2002, vol. 43, No. 4, pp. 1109-1115.
Dajcs JJ, et al., Effectiveness of Ciprofloxacin, Levofloxacin, or Moxifloxacin for Treatment of Experimental *Staphylococcus aureus* Keratitis, Antimicrobial Agents and Chemotherapy, 2004, vol. 48, No. 6, pp. 1948-1952.
Dajcs JJ, et al., Immunity to Lysostaphin and Its Therapeutic Value for Ocular MRSA Infections in the Rabbit, Invest Ophthalmol Vis. Sci, 2002, vol. 43, No. 12, pp. 3712-3716.
Dajcs JJ, et al., Lysostaphin treatment of methicillin-resistant *Staphylococcus aureus* keratitis in the rabbit, Investigative Ophthalmology & Visual Science, May 2000, vol. 41, No. 6, pp. 1432-1437.
Dajcs JJ, et al., The effectiveness of tobramycin and Ocuflox® in a prophylaxis model of *Staphylococcus* keratitis, Current Eye Resarch, 2001, vol. 23, No. 1, pp. 60-63.
Dajcs JJ, et al., Corneal Virulence of *Staphylococcus aureus* in an Experimental Model of Keratitis. DNA Cell Biol. 2002;21(5-6):375-382.

(56) References Cited

OTHER PUBLICATIONS

Dajcs, JJ et al., Effectiveness of Ciprofloxacin and Ofloxacin in a Prophylaxis Model of *Staphylococcus* Keratitis, Cornea, vol. 20, No. 8, 2004.

Deleo FR, Otto M. An antidote for *Staphylococcus aureus* pneumonia? J Exp Med. 2008;205(2):271-274.

Eichstaedt S, et al., Effects of *Staphylococcus aureus*-hemolysin A on calcium signaling in immortalized human airway epithelial cells. Cell Calcium. 2009, 45:165-176.

Girgis DO et al., Pathogenesis of *Staphylococcus* in the Rabbit Anterior Chamber, Investigative Ophthalmology & Visual Science, 2005, vol. 46.

Girgis DO, et al., Phospholipase A2 Activity in Normal and *Staphylococcus aureus*-Infected Rabbit Eyes, Investigative Ophthalmology & Visual Science, 2003, vol. 44, No. 1, 197-202.

Girgis DO, et al., Susceptibility of aged mice to *Staphylococcus aureus* keratitis, Current Eye Research, 2004, vol. 29, Nos. 4-5, pp. 269-275.

Girgis DO, et al., A New Topical Model of *Staphylococcus* Corneal Infection in the Mouse. Invest Ophthalmol Vis Sci. 2003;44(4):1591-1597.

Girgis DO, et al., Effects of Toxin Production in a Murine Model of *Staphylococcus aureus* Keratitis. Invest Ophthalmol Vis Sci. 2005;46, 1-7.

Gu LQ, et al., Interaction of the Noncovalent Molecular Adapter, 8-Cyclodextrin, with the Staphylococcal α-Hemolysin Pore. Biophys J 2000;79(4):1967-1975.

Hasliner B, et al., *Staphylococcus aureus* α-toxin induces apoptosis in peripheral blood mononuclear cells: role of endogenous tumor necrosis factor-α and the mitochondrial death pathway. Cell Microhiol. 2003;5(10):729-741.

Haslinger B, et al., Multiple virulence factors are required for *Staphylococcus aureus*-induced apoptosis in endothelial cells. Cell Microbial 2005:7(8):1087-1097.

Hume EB, et al., Immunization with Alpha-Toxin Toxoid Protects the Cornea against Tissue Damage During Experimental *Staphylococcus aureus* Keratitis. Infect Immun. 2000;68(10):6052-6055.

Hume EBH et al., Clarithromycin for experimental *Staphylococcus aureus* keratitis, Current Eye Research, 1999, vol. 18, No. 5, pp. 358-362.

Hume EBH et al., *Staphylococcus* Corneal Virulence in a New Topical Model of Infection, Investigative Ophthalmology & Visual Science, Nov. 2001, vol. 42, No. 12, pp. 2904-2908.

Insler MS et al., Successful Treatment of Methicillin-resistant *Staphylococcus aureus* Keratitis with Topical Ciprofloxacin, Ophthalmology, vol. 98, No. 11, Nov. 1991, pp. 1690-1692.

Karginov VA, et al. Inhibition of *S. aureus* α-hemolysin and *B. anthracis* lethal toxin by β-cyclodextrin derivatives. Bioorg Med Chem. 2007;15(16): 5424-5431.

Figure 1

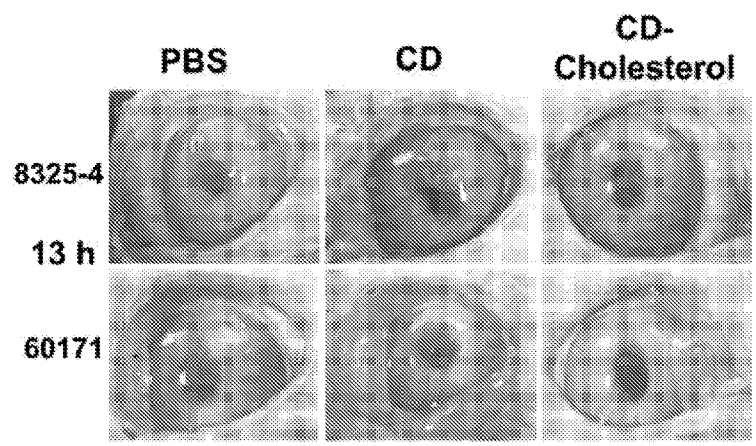
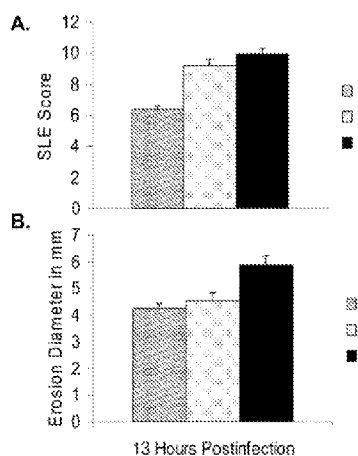
Figure 3
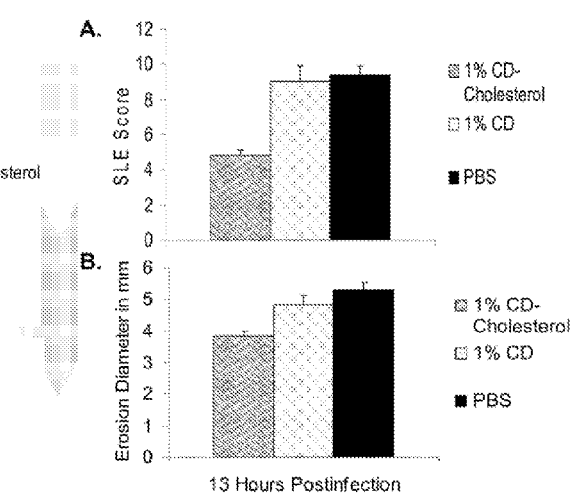
Figure 4
Figure 5

INHIBITORS OF ALPHA-TOXIN

PRIORITY INFORMATION

This invention claims benefit to U.S. Patent Application No. 61/175,385, filed May 4, 2009, the contents of which are incorporated herein by reference in their entirety.

FIELD OF THE INVENTION

The present invention relates to, generally, methods of treating, inhibiting, or ameliorating corneal damage during *Staphylococcus aureus* keratitis. α-Toxin mediates corneal damage during *Staphylococcus aureus* keratitis. Chemical inhibition of this toxin is sought to provide relief from toxin-mediated pathology.

BACKGROUND OF THE INVENTION

A gram-positive coccus, *Staphylococcus aureus* is one of the most important human pathogens. *S. aureus* causes a variety of infections with high morbidity and mortality including osteomyelitis, soft tissue infections, pneumonia, endocarditis, and brain abscesses. In the United States, there are approximately 292,000 hospital admissions of *S. aureus* infections annually. A survey showed that 19,000 people died in 2006 from *S. aureus* infections. To further intensify the scope of the problem, the rate of methicillin-resistant *S. aureus* isolates found both in the community and in hospitals is continuing to increase.

*S. aureus* is also a major cause of ocular infections, including blepharitis, conjunctivitis, keratitis, and endophthalmitis. Patients with these infections have intense pain, redness, and photophobia, and the infection can result in an ulcer with numerous infiltrating polymorphonuclear leukocytes. These infections can result in loss of visual acuity or blindness. Intensive antibiotic therapy can eradicate *S. aureus* from the infected site, but pathologic changes can continue due to action of toxic proteins that are secreted by *S. aureus*. The appearance of an infected eye may not be a good measure of the success of antibiotic treatment because the activity of the secreted toxins is not directly affected by the antibiotic-mediated killing of the bacteria.

A *S. aureus* protein that mediates ocular tissue damage is α-toxin. α-toxin has also been proven to have an important role in brain and respiratory infections caused by *S. aureus* and is being proposed as a vaccine target for humans. α-toxin is a 33 kDa protein that forms a ring of seven α-toxin molecules that penetrate the host cell membrane forming a pore, causing cell lysis. α-toxin has also been demonstrated to cause cellular changes in human cells, upregulate inflammatory cytokines, cause calcium disruptions reducing host defenses, and cause apoptosis. Furthermore, α-toxin has been shown to be an important virulence factor in both rabbit and murine models of keratitis. When the α-toxin gene was mutated, the pathology associated with the infection was significantly reduced compared to the parent strain. However, when the mutated α-toxin gene in the knockout strain was complemented, the pathology was restored.

To date, there are no known inhibitors of α-toxin available to treat *S. aureus* infection, including ocular infections. There have been efforts to develop inhibitors of this important virulence factor including the use of steroids or steroid-like molecules. It has been demonstrated that α-toxin binds to caveolin, a protein present in lipid rafts. α-toxin has a caveolin-1 binding motif that, when removed, results in a nonhemolytic form of α-toxin. Peptides that mimic the caveolin-binding domain of α-toxin have been shown to limit the action of α-toxin on cell membranes. It has been shown that methyl-β-cyclodextrin (CD) can bind weakly to the pore of α-toxin heptamer. On introducing amino acid changes in the α-toxin, Gu et al. were able to increase the binding of CD. Furthermore, Vijayvargia et al. observed that cholesterol depletion of cells arrested the action of α-toxin and that chelation of cholesterol, using CD, helped retard the pore formation by α-toxin. Karginov et al. have demonstrated that α-toxin action can be inhibited by positively charged side groups chemically attached to CD.

Embodiments of the present invention show that a complex of cholesterol and CD (CD-cholesterol) can inhibit the action of α-toxin. The results show that CD-cholesterol complex can inhibit α-toxin action in vitro and in vivo.

SUMMARY OF THE INVENTION

One embodiment of the present invention is a method for inhibiting damage to a mammalian cornea, comprising administering an effective α-toxin inhibiting about of a composition that comprises a β-cyclodextrin and cholesterol. In other aspects of the invention, this compositions comprises a pharmaceutical carrier.

In other aspects of the invention, the composition includes a cholesterol or cholesterol solution, and a β-cyclodextrin or β-cyclodextrin solution.

In another aspect of the invention, the cholesterol solution further comprises a pharmaceutical carrier, and the β-cyclodextrin solution further comprises a pharmaceutically acceptable carrier.

Another embodiment of the present invention is a pharmaceutical composition comprising 0.1% w/v to about 5% w/v cholesterol, 0.1 w/v to about 5% w/v methyl-β-cyclodextrin, and a pharmaceutically acceptable carrier.

In another aspect of the invention, the composition further comprises a steroid and/or an antibiotic.

Embodiments of the present invention show that inhibition of rabbit erythrocyte lysis by α-toxin can be inhibited by CD plus cholesterol (0.1%, CD-cholesterol). As demonstrated in the Example section below, pathologic changes in rabbit corneas injected with 12 hemolytic units of α-toxin suspended in PBS, 1% CD, or 1% CD-cholesterol were compared over time. Rabbit corneas injected with $10^2$ colony forming units (CFU) of *S. aureus* were treated from 7 to 13 hours postinfection (PI) with a total of 15 drops of CD-cholesterol, CD, or PBS. Slit lamp examination (SLE) and measurement of erosions were performed at 13 hours PI and bacteria were quantified at 14 hours PI.

The Example showed that toxin-mediated lysis of erythrocytes was inhibited in vitro up to 16,000-fold in the presence of CD-cholesterol compared with CD or PBS. Eyes injected with α-toxin mixed with CD-cholesterol had, at 7 hours postinjection, significantly smaller erosions than eyes injected with α-toxin in PBS or α-toxin mixed with CD (P=0.0090 and P=0.0035, respectively). Eyes infected with *S. aureus* and treated with CD-cholesterol had significantly lower SLE scores than eyes treated with CD or PBS (P≤0.0103 and P≤0.0017, respectively); however, there were no differences in the number of bacteria present (P≥0.0648).

Other embodiments of the present invention will be well understood by one of ordinary skill in the art when reviewing the instant specification. In summary, embodiments of the present invention show that the CD-cholesterol matrix of the present invention is a potent inhibitor of α-toxin activity in vitro and an effective means to arrest corneal damage during *S. aureus* keratitis.

BRIEF DESCRIPTION OF THE FIGURES

FIG. 1 show an in vitro analysis of α-toxin inhibition with 0.1% CD-cholesterol, or 0.1% CD. Rabbit erythrocytes ($10^8$ per mL) were either incubated with 0.1% CD-cholesterol, 0.1% CD, or untreated for 30 minutes at 4° C. Serial dilutions (1:2) of α-toxin were made in microtiter plates. Aliquots of erythrocytes were added to each well ($10^7$ per well). Untreated erythrocytes were suspended in PBS with 0.02% gelatin to serve as a negative control. (A) Untreated erythrocytes were incubated with α-toxin. The hemolytic titer of the α-toxin was 4096. (B) Erythrocytes treated with 0.1% CD did not demonstrate a significant reduction in α-toxin titer compared with the negative control, a two-fold reduction. (C) The hemolytic titer of α-toxin was reduced from 4096 to 4 when the red blood cells were incubated with 0.1% CD-cholesterol, a reduction of approximately 500-fold. (D) Erythrocytes were incubated with α-toxin at an increased concentration. The hemolytic titer was 65,536. (E) Erythrocytes were incubated with 0.1% CD-cholesterol, but with an increased concentration of α-toxin. The hemolytic titer was reduced from 65,536 to 4, a reduction of approximately 16,000.

FIG. 3 is a set of photographs of rabbit corneas infected with *S. aureus* and treated with 1% CD-cholesterol, 1% CD, or PBS. Rabbit corneas were injected with $10^2$ CFU of *S. aureus* 8325-4 or 60171. Treatments began at 7 hours PI until 13 hours PI. A single topical drop was applied every 15 minutes between 7 and 8 hours PI. Starting at 8.5 hours, drops were applied every 30 minutes until 13 hours PI. At 13 hours PI, photographs were taken to record the degree of pathologic change.

FIG. 4 is a set of graphs that show the effect of CD-cholesterol treatment of eyes infected with strain 8325-4. Rabbit corneas were injected with $10^2$ CFU of *S. aureus* 8325-4. Eyes were randomized and treated with 1% CD-cholesterol, 1% CD, or PBS from 7 to 13 hours PI. At 7 hours PI, eyes were treated with a single topical drop every 15 minutes from 7 to 8 hours PI. At 8.5 hours PI, eyes were treated with a single topical drop every 30 minutes until 13 hours PI (a total of 15 drops). At 13 hours PI, the eyes were evaluated by SLE (A) and erosion diameters were measured using fluorescein strips (B) The pathologic changes were observed then averaged and statistical comparisons were performed using one-way ANOVA. The erosions were averaged and statistical comparisons using analysis of variance and Student's t-test were performed. Error bars are the standard error of the mean (SEM). P≤0.05, for either test, was considered significant. (A) Eyes treated with CD-cholesterol had a significantly lower SLE score than either the eyes treated with 1% CD or with PBS (P=0.0103 and P=0.0017, respectively). The eyes treated with 1% CD or with PBS had statistically similar SLE scores (P=0.4002). (B) The eyes treated with 1% CD-cholesterol or 1% CD had significantly smaller erosions than the PBS treated eyes (P=0.0017 and P=0.0103, respectively). The eyes treated with 1% CD-cholesterol or 1% CD had erosion diameters similar to one another (P=0.4002).

FIG. 5 is a set of graphs that show the effect of CD-cholesterol treatment of eyes infected with strain 60171. Eyes were treated and evaluated as described for FIG. 3. Error bars are the SEM. (A) Eyes treated with CD-cholesterol had significantly lower SLE scores than either the eyes treated with 1% CD or PBS (P=0.0013, or P<0.0001, respectively). In contrast, the CD-treated eyes had similar SLE scores compared to the PBS-treated eyes (P=0.7403). (B) The eyes treated with 1% CD-cholesterol had significantly smaller erosions than either the eyes treated with 1% CD alone or the eyes treated with PBS (P=0.0220 and P=0.0003, respectively). There was no statistical difference between the eyes treated with 1% CD and the eyes treated with PBS (P=0.2131).

DESCRIPTION OF THE INVENTION

Figure 2:
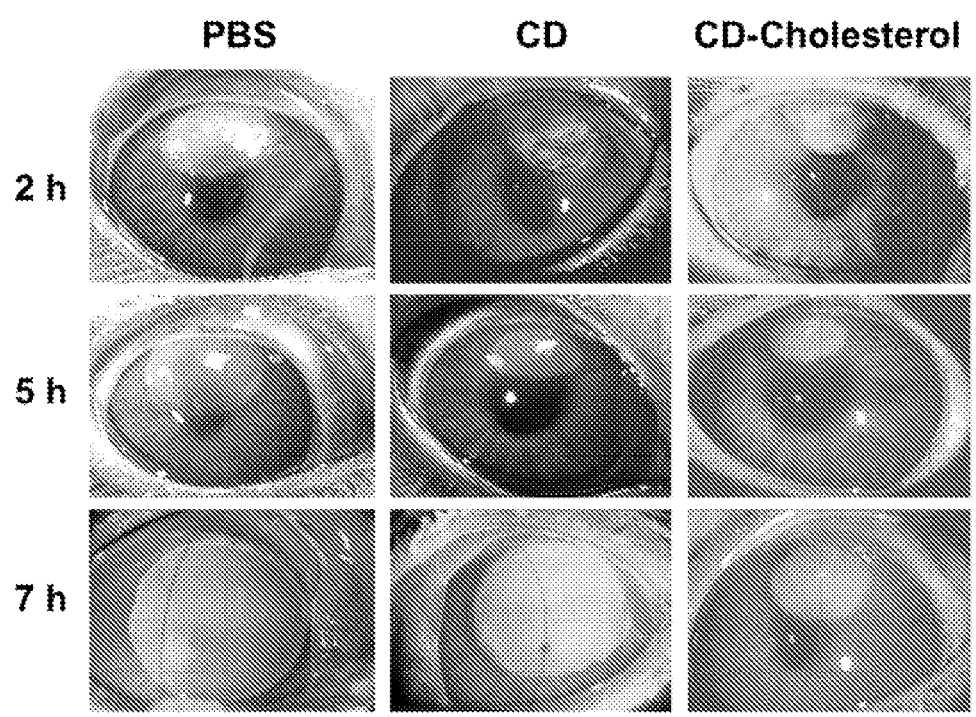
FIG. 2 is a set of photographs of rabbit corneas injected with α-toxin. Rabbit corneas (n≥4 corneas per group) were injected with 12 hemolytic units of α-toxin suspended in 1% CD-cholesterol, 1% CD, or PBS. At 2, 5, and 7 hours postinjection, erosions were stained with fluorescein and measured. Eyes injected with α-toxin suspended in CD-cholesterol had small erosions compared with α-toxin-injected eyes. CD afforded some protection from large erosion formation for a short time, but by 5 hours postinjection the CD failed to protect the cornea and the erosion formation was similar to the erosions diameters of the eyes injected with α-toxin mixed with PBS.

Embodiments of the present invention show that CD-cholesterol is an effective inhibitor of α-toxin that can block the lytic action on erythrocytes and, more importantly, protect the cornea and tissues from toxin action during infection or when α-toxin is injected into the cornea. CD-cholesterol limited pathologic effects on infected eyes, but did not reduce growth of infecting bacteria. Without being bound by theory or mechanism, this implies that CD-cholesterol inhibition of α-toxin achieved an effective therapy of the infected eyes despite the continued growth of bacteria and the continuing production of α-toxin. CD-cholesterol inhibition of α-toxin was not strain specific; that is, the inhibitor was active for commercial toxin as well as toxin produced by a variety of strains, including ocular clinical isolates (see Table 1, below).

The mechanism by which CD-cholesterol inhibits α-toxin has not yet been demonstrated. The very general terms, Raff et al. previously demonstrated that α-toxin activity was weakly inhibited by a high concentration of hydrocortisone or methylprednisolone. It has been determined that caveolin, as found in lipid rafts, is an important glucocorticosteroid receptor that could bind molecules like methylprednisolone, hydrocortisone, or, in the present invention, cholesterol. Others have demonstrated that α-toxin activity is dependent on caveolin-1. It has also been demonstrated that α-toxin activity on cells can be delayed by sequestering cholesterol, or inhibited altogether when cholesterol is depleted from cells. Therefore, without being bound by theory or mechanism, a possible mechanism for the effectiveness of CD-cholesterol as an inhibitor of α-toxin could be that CD-cholesterol competes for the same cellular target as α-toxin. This competitive binding to the cellular target molecule would reduce the number of caveolin molecules available to α-toxin resulting in fewer cells being lysed as a consequence of α-toxin pore formation. Alternatively, CD-cholesterol could bind to the toxin and interfere with its lytic and cytotoxic activities.

There have also been reports of α-toxin inhibition by modified CD, showing that hepta-6-substituted CD molecules can create a molecule that interferes with the lytic action of the toxin. These modified CD molecules are thought to have affinity for the α-toxin heptamer. Specifically, the modified CD molecules are thought to occlude the central pore of the toxin.

The CD molecule alone had variable effects on the action of α-toxin. In the in vitro hemolysis assay, CD alone failed to significantly inhibit the hemolytic action of α-toxin. In contrast, when CD was mixed with α-toxin then injected into rabbit corneas, there were some protective effects mediated by CD; that is, at 2 hours postinjection the corneas showed staining with fluorescein, but the epithelium was still intact. The fluorescein had penetrated under the epithelial layer suggesting that the layer had been partially loosened by the toxin. However, at 5 hours postinjection, the eyes developed erosions comparable to eyes injected with toxin mixed with PBS. Furthermore, the application of CD alone to eyes infected with *S. aureus* 8325-4 reduced the size of corneal erosions, but CD alone did not reduce the overall SLE score. These findings can be understood if one considers that, in the eye, the CD molecule can react with cholesterol or other lipid present in the tear film or surrounding tissues to form a complex that has significant inhibitory action on α-toxin. Because of the greater availability of lipids in the eye (e.g., tear film) than in the erythrocyte lysis assay, such spontaneous formation of an inhibitory complex could be more likely to occur in vivo than in the erythrocyte suspension used for the hemolysis assays in vitro.

α-toxin, as has been demonstrated by virulence studies of bacterial mutants in rabbits and mice, can cause the majority of the pathologic changes observed during ocular infection. Studies with purified α-toxin injected into rabbit corneas show that nanogram quantities of α-toxin are toxic. α-toxin is produced in readily detectable quantities by most *S. aureus* isolates. Strain Newman was reportedly deficient in α-toxin production, but more recent studies showed that the very small amount of α-toxin produced by this strain made a significant contribution to its virulence in the rabbit cornea. Additional findings on the importance of α-toxin to corneal virulence have been obtained through the study of α-toxin neutralizing antibody. Neutralizing antibody was capable of inhibiting the damage associated with α-toxin during keratitis infection without affecting the growth of bacteria. Although examples of the present invention were performed in a rabbit model of keratitis, one of ordinary skill in the art would understand that the action of α-toxin on human cells is very similar to its action on rabbit cells indicating that the results could be relevant to humans.

Based on the demonstrated importance of α-toxin to keratitis, the treatment of *Staphylococcus* keratitis with an inhibitor of α-toxin is a valuable adjunctive therapy that could potentially limit corneal damage while an antibiotic therapy kills the infecting bacteria. The inhibition of α-toxin activity could be especially beneficial in those cases in which the antibiotic therapy is slow or ineffective at killing the infecting bacteria in the cornea.

Thus, one embodiment of the present invention relates to a method for treating, inhibiting, or ameliorating corneal damage during *Staphylococcus aureus* keratitis comprising administering, to a subject in need of treatment thereof, an effective amount of an active ingredient comprising CD and cholesterol. The compositions of the present invention may be combined with a pharmaceutically acceptable carrier for delivery to the eye.

Dosages and administration for the therapeutic agents of the present invention include amounts that will be effective in preventing or treating corneal damage, and one would readily recognize that this amount will vary greatly depending on the nature of the cornea and the condition of a patient.

An example of the cholesterol that can be used in connection with the present invention is C75209, available from Sigma-Aldrich. Additionally, the cholesterol may be soluble in the composition of the present invention. Alternatively, the cholesterol may be encapsulated. Others of course would be known to one of ordinary skill in the art.

In embodiments of the present invention, the cholesterol is in a solution containing between about 0.1% w/v cholesterol and about 99.9% w/v cholesterol. In other embodiments, the cholesterol is in a solution containing between about 0.5% w/v cholesterol and about 5% w/v cholesterol. In other embodiments, the cholesterol is in a solution containing about 1% w/v cholesterol. In other embodiments, the cholesterol is in a solution containing about 5%, 10%, 15%, 20%, 25%, 30%, 35%, 40%, 45%, 50%, 55%, 60%, 65%, 70%, 75%, 80%, 85%, 90%, 95%, or higher.

Examples of the cyclodextrin that can be used in connection with the present invention include cyclodextrins may be used, including randomly methylated-β-cyclodextrin, 2-hydroxypropyl-β-cyclodextrin, and sulfobutylether-β-cyclodextrin. A preferred example is methyl β-cyclodextrin.

In embodiments of the present invention, the cyclodextrin is in a solution containing between about 0.1% w/v cyclodextrin and about 99.9% w/v cyclodextrin. In other embodiments, the cyclodextrin is in a solution containing between about 0.5% w/v cyclodextrin and about 5% w/v cyclodextrin. In other embodiments, the cyclodextrin is in a solution containing about 1% w/v cyclodextrin. In other embodiments, the cyclodextrin is in a solution containing about 5%, 10%, 15%, 20%, 25%, 30%, 35%, 40%, 45%, 50%, 55%, 60%, 65%, 70%, 75%, 80%, 85%, 90%, 95%, or higher.

As examples of the present invention, the cholesterol or cholesterol solution are in a complex or formulation with the cyclodextrin or cyclodextrin solution. The cholesterol solution may comprise about 0.01% to about 95% of the complex or CD-cholesterol composition of the present invention. In other embodiments of the present invention, the cholesterol solution may comprise about 0.01% to about 5% of the complex or CD-cholesterol composition. The cyclodextrin may comprise about 0.01% to about 5% of the complex or CD-cholesterol composition of the present invention.

The CD-cholesterol composition is then formed into a pharmaceutically acceptable composition. Alternatively or additionally, at least one pharmaceutical carrier is added to the cholesterol solution and/or the cyclodextrin composition. These aspects of the present invention are further described below.

An "effective amount" of the therapeutic agent or pharmaceutical agent to be used in accordance with the invention is intended to mean a nontoxic but sufficient amount of the agent, such that the desired prophylactic or therapeutic effect is produced. Thus, the exact amount of the therapeutic or a particular agent that is required will vary from subject to subject, depending on the species, age, and general condition of the subject, the severity of the condition being treated, the particular carrier or adjuvant being used and its mode of administration, and the like. Similarly, the dosing regimen should also be adjusted to suit the individual to whom the composition is administered and will once again vary with age, weight, metabolism, etc. of the individual. Accordingly, the "effective amount" of any particular therapeutic composition will vary based on the particular circumstances, and an appropriate effective amount may be determined in each case of application by one of ordinary skill in the art using only routine experimentation.

Additionally, according to the present invention, the drugs can be applied systemically or topically. Usually, the compound may be administered by oral administration, intranasal administration, inhalational administration, intravenous injection (including infusion), subcutaneous injection, transdermal administration, eye local administration (e.g. periocular (subtenon's), subconjunctival, intraocular, intravitreal, intracameral, subretinal, suprachoroidal, and retrobulbar administrations) and the like.

Of course, the dose may vary depending on the strain of the mammal, age, body weight, symptom to be treated, desired therapeutic effect, administration route, term of treatment and the like.

The compositions of the present invention may further contain physiologically acceptable additives. Said additives may include the ingredients used with the present compounds such as excipient, diluent, filler, resolvent, lubricant, adjuvant, binder, disintegrator, coating agent, cupsulating agent, ointment base, suppository base, aerozoling agent, emulsifier, dispersing agent, suspending agent, thickener, tonicity agent, buffering agent, soothing agent, preservative, antioxidant, corrigent, flavor, colorant, a functional material such as cyclodextrin and biodegradable polymer, stabilizer. The additives are well known to the art and may be selected from those described in general reference books of pharmaceutics.

Examples of solid compositions for oral administration include tablets, troches, sublingual tablets, capsules, pills, powders, granules and the like. The solid composition may be prepared by mixing one or more active ingredients with at least one inactive diluent. The composition may further contain additives other than the inactive diluents, for example, a lubricant, a disintegrator and a stabilizer. Tablets and pills may be coated with an enteric or gastroenteric film, if necessary.

Examples of liquid compositions for oral administration include emulsions, solutions, suspensions, syrups and elixirs and the like. Said composition may further contain a conventionally used inactive diluents (e.g. purified water or ethyl alcohol). The composition may contain additives other than the inactive diluents such as adjuvant (e.g. wetting agents and suspending agents, sweeteners, flavors, fragrance and preservatives).

The composition of the present invention may be in the form of spraying composition, which contains one or more active ingredients and may be prepared according to a known method.

Examples of injectable compositions of the present invention for parenteral administration include sterile aqueous or non-aqueous solutions, suspensions and emulsions. Diluents for the aqueous solution or suspension may include, for example, distilled water for injection, physiological saline and Ringer's solution. Non-aqueous diluents for solution and suspension may include, for example, propylene glycol, polyethylene glycol, vegetable oils such as olive oil, alcohols such as ethanol and polysorbate. The composition may further comprise additives such as preservatives, wetting agents, emulsifying agents, dispersing agents and the like. They may be sterilized by filtration through, (e.g. a bacteria-retaining filter, compounding with a sterilizer, or by means of gas or radioisotope irradiation sterilization).

The injectable composition may also be provided as a sterilized powder composition to be dissolved in a sterilized solvent for injection before use.

Examples of external agent include all the external preparations used in the fields of dermatology and otolaryngology, which includes ointment, cream, lotion and spray.

The present composition is also applied by means of ophthalmic solution, eye drop, eye ointment and the like. The form includes all the formulations for eye local administration used in the ophthalmic field.

The ophthalmic solution or eye drops are prepared by dissolving active ingredients in a sterile aqueous solution such as saline and buffering solution, or by combining powder compositions to be dissolved before use. The eye ointments are prepared by mixing the active ingredient into the base. The formulations may be prepared according to any of the conventional methods.

Osmolarity modifiers may be any of those ordinarily used in the ophthalmic field. Examples of osmolarity modifiers include, but not limited thereto, sodium chloride, potassium chloride, calcium chloride, sodium bicarbonate, sodium carbonate, magnesium sulfate, sodium hydrogen phosphate, sodium dihydrogen phosphate, dipotassium hydrogen phosphate, boric acid, borax, sodium hydroxide, hydrochloric acid, mannitol, isosorbitol, propylene glycol, glucose and glycerineas.

Further, additives ordinarily used in the ophthalmic field may be added to the present composition as desired. Such additives include, for example, buffer agent (e.g., boric acid, sodium monohydrogen phosphate and sodium dihydrogen phosphate), preservatives (e.g., benzalkonium chloride, benzethonium chloride and chlorobutanol), thickeners (e.g., saccharide, such as lactose and mannitol, maltose; e.g., hyaluronic acid or its salt such as sodium hyaluronate and potassium hyaluronate; e.g., mucopolysaccharide such as chondroitin sulfate; e.g., sodium polyacrylate, carboxyvinyl polymer and crosslinked polyacrylate), all of which are included herein by reference.

In preparing the present composition as an eye ointment, other than the above additives, the composition may contain ordinarily used eye ointment base. Such eye ointment base includes, but not limited to, oil base such as vaseline, liquid paraffin, polyethylene, selen 50, plastibase, macrogol or a combination thereof; emulsion base having oil phase and water phase emulsified with surfactant; and water soluble base such as hydroxypropylmethylcellulose, carboxypropylmethylcellulose, and polyethylene glycol.

The term "treatment" or "treating" used herein includes any means of control of the disease or condition, such as prevention, care, relief of the condition, attenuation of the condition and arrest of progression. The term "ameliorate" refers to a decrease or lessening of the symptoms or signs of the disorder being treated. The symptoms or signs that may be ameliorated include those associated with damage to the mammalian cornea.

The term "inhibition" or "inhibiting" refers to the reduction or suppression of a given condition, symptom, or disorder, or disease, or a significant decrease in the baseline activity of a biological activity or process. Preferably, the condition or symptom or disorder or disease is associated with α-toxin damage during infection.

Additionally, in other embodiments of the present invention, the formulations may be administered by an ocular route, such as topical, subconjunctival, sub-tenon, intraocular, etc. Moreover the formulation may be administered as a slow release formulation, with a carrier formulation such as nanospheres, nanocapsules, microspheres, microcapsules, liposomes, etc., as an intravenous solution or suspension, or in an intraocular injection, as known to one skilled in the art. A time-release drug delivery system may be administered intraocularly to result in sustained release of the agent over a period of time. The formulation may be in the form of a vehicle, such as a micro- or macro-capsule or matrix of biocompatible polymers such as polycaprolactone, polyglycolic acid, polylactic acid, polyanhydrides, polylactide-co-glycolides, polyamino acids, polyethylene oxide, acrylic terminated polyethylene oxide, polyamides, polyethylenes, polyacrylonitriles, polyphosphazenes, poly(ortho esters), sucrose acetate isobutyrate (SAIB), and other polymers such as those disclosed in U.S. Pat. Nos. 6,667,371; 6,613,355; 6,596,296;

6,413,536; 5,968,543; 4,079,038; 4,093,709; 4,131,648; 4,138,344; 4,180,646; 4,304,767; 4,946,931, each of which is expressly incorporated by reference herein in its entirety, or lipids that may be formulated as microspheres or liposomes. A microscopic or macroscopic formulation may be administered through a needle, or may be implanted by suturing within the eye, for example, within the lens capsule. Delayed or extended release properties may be provided through various formulations of the vehicle (coated or uncoated microsphere, coated or uncoated capsule, lipid or polymer components, unilamellar or multilamellar structure, and combinations of the above, etc.). The formulation and loading of microspheres, microcapsules, liposomes, etc. and their ocular implantation are standard techniques known by one skilled in the art, for example, the use a ganciclovir sustained-release implant to treat cytomegalovirus retinitis, disclosed in Vitreoretinal Surgical Techniques, Peyman et al., Eds. (Martin Dunitz, London 2001, chapter 45); Handbook of Pharmaceutical Controlled Release Technology, Wise, Ed. (Marcel Dekker, New York 2000), the relevant sections of which are incorporated by reference herein in their entirety. For example, a sustained release intraocular implant may be inserted through the pars plana for implantation in the vitreous cavity. An intraocular injection may be into the vitreous (intravitreal), or under the conjunctiva (subconjunctival), or behind the eye (retrobulbar), or under the Capsule of Tenon (sub-Tenon), and may be in a depot form. Other intraocular routes of administration and injection sites and forms are also contemplated and are within the scope of the invention.

For example, the formulation is intraocularly injected, for example, into the vitreous. When administering the formulation by intravitreal injection, the active agents should be concentrated to minimise the volume for injection.

There are several examples of sub-tenon delivery that can be used in connection with the present invention. For example, a straight, 5/8 inch long, 25 gauge needle to perform sub-tenon injection of corticosteroids for the treatment of posterior uveitis or macular edema associated with uveitis or anterior segment surgery. See Uveitis: A Clinical Approach to Diagnosis and Management (Second Edition), Ronald E. Smith and Robert A. Nozik, 1989, pp. 63-68; "Echographic Localization of Corticosteroids After Periocular Injection", William R. Freeman, Ronald L. Green, and Ronald E. Smith, American Journal of Ophthalmology 103:281-288, March 1987.

It is also known to use a blunt cannula having to perform sub-Tenon injection of anesthesia for cataract and vitreoretinal surgery. See "Local Anesthesia for Vitreoretinal Surgery", Calvin E. Mein and Michael G. Woodcock, Retina 10: 47-49, 1990; "Ocular Anesthesia for Cataract Surgery: A Direct Sub-Tenon's Approach", Ophthalmic Surgery 21:696-699, 1990; "Single Quadrant Sub-Tenon's Bock: Evaluation of a New Local Anaesthetic Technique for Eye Surgery", Anaesthesia and Intensive Care 24: 241-244, April 1996.

It is also known to use a gently curved cannula. See "Curved, SubTenon Cannula for Local Anesthesia", Julian D. Stevens, Ophthalmic Surgery, 24:121-122, February 1993. Also see "A Modified Sub-Tenon's Cannula for Local Anesthesia", P. Muthusamy and Richard F. Hommersom, Asia-Pacific Journal of Ophthalmology, Volume 8, No. 3 (July 1996).

One example of sub-tenon delivery is disclosed in U.S. Pat. No. 6,413,245, incorporated herein by reference. In this embodiment, a formulation of the present invention a cannula as described in U.S. Pat. No. '245 is inserted below the Tenon's capsule and above the sclera of the human eye at a point posterior to a limbus of the eye. This example of a cannula includes a distal portion having a radius of curvature substantially equal to a radius of curvature of the globe of the human eye. A composition of the present invention is injected through the cannula to form a drug depot on an outer surface of the sclera.

In embodiments, for exemplary purposes, in preparation for injection, topical alcaine may be applied to the ocular surface, followed by 5% povidone iodine. A cotton-tipped applicator soaked in 4% lidocaine can then applied to the injection site, which is 4.0 mm posterior to the limbus in phakic eyes and 3.5 mm posterior to the limbus in pseudophakic eyes. A 27-gauge needle is used for injection at the superior pars plana. Indirect ophthalmoscopy can be used to confirm proper intravitreal placement of the suspension.

A syringe that can be used with this example is one which can accommodate a 21 to 30 gauge needle (eg a 23, 24, 25, 26 or 27 gauge needle) and is preferably of a small volume, for example 1.5 mL, or more preferably 0.5 mL. Although it is possible that the needle and syringe may be of the type where the needle is removable from the syringe, it is preferred that the arrangement is of a unitary syringe/needle construction. This would clearly limit the possibility of disengagement of the needle from the syringe. It is also preferred that the arrangement be tamper evident. The formulations of the present invention may therefore be provided in the form of a single unit dose in a pre-prepared syringe, ready for administration.

A suitable style of syringe is, for example, sold under the name of Uniject™ manufactured by Becton Dickinson and Company. In this style of syringe, the material is expelled through the needle into the eye by pressure applied to the sides of a pliable reservoir supplying the needle, rather than by a plunger. As the name implies, the construction of the reservoir and needle forms a single unit.

Topical application of formulations of the invention may be as an in situ gellable aqueous formulation. Such a formulation comprises a gelling agent in a concentration effective to promote gelling upon contact with the eye or with lacrimal fluid in the exterior of the eye. Suitable gelling agents include, but are not limited to, thermosetting polymers such as tetra-substituted ethylene diamine block copolymers of ethylene oxide and propylene oxide (e.g., poloxamine); polycarbophil; and polysaccharides such as gellan, carrageenan (e.g., kappa-carrageenan and iota-carrageenan), chitosan and alginate gums.

The phrase "in situ gellable" as used herein embraces not only liquids of low viscosity that form gels upon contact with the eye or with lacrimal fluid in the exterior of the eye, but also more viscous liquids such as semi-fluid and thixotropic gels that exhibit substantially increased viscosity or gel stiffness upon administration to the eye. Indeed, it can be advantageous to formulate a formulation of the invention as a gel, to minimize loss of the formulation immediately upon administration, as a result, for example, of lacrimation caused by reflex blinking Although it is preferred that such a formulation exhibit further increase in viscosity or gel stiffness upon administration, this is not absolutely required if the initial gel is sufficiently resistant to dissipation by lacrimal drainage to provide the effective residence time specified herein.

To prepare an example of a topical formulation for the present invention, a therapeutically effective amount of the CD/cholesterol formulation of the invention is placed in an ophthalmological vehicle as is known in the art. The amount of the therapeutic formulation to be administered and the concentration of the compound in the topical formulations depend upon the diluent, delivery system or device selected, the clinical condition of the patient, the side effects and the stability of the compound in the formulation. Thus, the physician employs the appropriate preparation containing the appropriate concentration of the therapeutic compound and selects the amount of formulation administered, depending upon clinical experience with the patient in question or with similar patients.

Where the formulation contains two or more active agents, the active agents may be administered as a mixture, as an admixture, in the same formulation, in separate formulations, in extended release formulations, liposomes, microcapsules, or any of the previously described embodiments.

Importantly, the method of the present invention may be performed alone, or in combination with one or more other therapies such as photodynamic therapy, laser treatment, or one or more biological or pharmaceutical treatments such as a steroidal or anti-infective treatment.

For example, the formulations prepared according to the present invention may be prepared in combination with a glucocorticoid (e.g. prednisolone, prednisone), an oestrogen (e.g. oestrodiol), an androgen (e.g. testosterone) retinoic acid derivatives (e.g. 9-cis-retinoic acid, 13-trans-retinoic acid, all-trans retinoic acid), a vitamin D derivative (e.g. calcipotriol, calcipotriene), a non-steroidal anti-inflammatory agent, a vitamin D derivative, an anti-infective agent, a protein kinase C inhibitor, a MAP kinase inhibitor, an anti-apoptotic agent, a growth factor, a nutrient vitamin, an unsaturated fatty acid, and/or ocular anti-infective agents, for the treatment of the ophthalmic disorders set forth herein. In still other embodiments of the invention, a mixture of these agents may be used.

Examples of ocular anti-infective agents as described herein include, but are not limited to, penicillins (ampicillin, aziocillin, carbenicillin, dicloxacillin, methicillin, nafcillin, oxacillin, penicillin G, piperacillin, and ticarcillin), cephalosporins (cefamandole, cefazolin, cefotaxime, cefsulodin, ceftazidime, ceftriaxone, cephalothin, and moxalactam), fluroquinolones (ciprofloxacin, levofloxacin, gatifloxacin, and moxifloxacin), aminoglycosides (amikacin, gentamicin, netilmicin, tobramycin, and neomycin), miscellaneous agents such as aztreonam, bacitracin, ciprofloxacin, clindamycin, chloramphenicol, cotrimoxazole, fusidic acid, imipenem, metronidazole, teicoplanin, and vancomycin), antifungals (amphotericin B, clotrimazole, econazole, fluconazole, flucytosine, itraconazole, ketoconazole, miconazole, natamycin, oxiconazole, and terconazole), antivirals (acyclovir, ethyldeoxyuridine, foscarnet, ganciclovir, idoxuridine, trifluridine, vidarabine, and (S)-1-(3-dydroxy-2-phospho-nyluethoxypropyl) cytosine (HPMPC), antineoplastic agents (cell cycle (phase) nonspecific agents such as alkylating agents (chlorambucil, cyclophosphamide, mechlorethamine, melphalan, and busulfan), anthracycline antibiotics (doxorubicin, daunomycin, and dactinomycin), cisplatin, and nitrosoureas), antimetabolites such as antipyrimidines (cytarabine, fluorouracil and azacytidine), antifolates (methotrexate), antipurines (mercaptopurine and thioguanine), bleomycin, vinca alkaloids (vincrisine and vinblastine), podophylotoxins (etoposide (VP-16)), and nitrosoureas (carmustine, (BCNU)), immunosuppressant agents such as cyclosporin A and SK506, and anti-inflammatory or suppressive factors (inhibitors), and inhibitors of proteolytic enzymes such as plasminogen activator inhibitors. Doses for topical and sub-conjunctival administration of the above agents, as well as intravitreal dose and vitreous half-life may be found in Intravitreal Surgery Principles and Practice, Peyman G A and Shulman, J Eds., 2nd edition, 1994, Appleton-Longe, the relevant sections of which are expressly incorporated by reference herein.

One example of delivery is the use of compositions of the present invention with the ophthalmic liposome composition of United States Patent Application Number 2004/0224010. Thus, in one aspect, the present invention provides a lipid formulation, the lipid formulation comprising: a lipid phase, the lipid phase comprising a neutral lipid and a member selected from the group consisting of a cationic lipid and a mucoadhesive compound; an aqueous phase; and a therapeutic agent. In one embodiment, the lipid formulation is a liposome, a nanocapsule, a microparticle, a microsphere, a lipid complex, and the like. In another embodiment, the lipid formulation is a liposome and the therapeutic agent is encapsulated in or associated with the liposome. Also, the lipid phase comprises a neutral lipid as well as a cationic lipid or a mucoadhesive compound. Suitable neutral lipids include any of a number of lipid species which exist either in an uncharged or neutral zwitterionic form at physiological pH.

Such neutral lipids include, but are not limited to, phospholipids, such as phosphatidylcholine, sphingomyelin, phosphatidylethanolamine, phosphatidylserine, phosphatidylinositol, phosphatidic acid, palmitoyloleoyl phosphatdylcholine, lysophosphatidylcholine, lysophosphatidylethanolamine, dipalmitoylphosphatidylcholine, dioleoylphosphatidylcholine, distearoylphosphatidylcholine and dilinoleoylphosphatidylcholine. In a preferred embodiment, the neutral lipid is a phosphatidylcholine, such as Phospholipon 90H, Phospholipon 80H or a mixture thereof. In another embodiment the phosopholipid includes, but is not limited to, phosphatidyl choline (PC), lyso-phosphatidyl choline (1-PC), phosphatidyl serine (PS), phosphatidyl ehtanolamine (PE), phosphatidyl glycerol (PG), and phosphatidyl inisotol (PI). Suitable cationic lipids include those that carry a net positive charge at physiological pH. Such cationic lipids include, but are not limited to, N,N-dioleyl-N,N-dimethylammonium chloride ("DODAC"); N-(2,3-dioleyloxy)propyl-N, N—N-triethylammonium chloride ("DOTMA"); N,N-distearyl-N,N-dimethylammonium bromide ("DDAB"); N-(2, 3-dioleoyloxy)propyl)-N,N,N-trimethylammonium chloride ("DOTAP"); 3.beta.-(N—(N',N'-dimethylaminoethane)-carbamoyl)cholesterol ("DC-Chol"), N-(1-(2,3-dioleyloxy)propyl)-N-2-(sperminecarboxamido)ethyl)-N,N-dimethyl-ammonium trifluoracetate ("DOSPA"), dioctadecylamidoglycyl carboxyspermine ("DOGS"), 1,2-dileoyl-sn-3-phosphoethanolamine ("DOPE"); N-(1,2-dimyristyloxyprop-3-yl)-N,N-dimethyl-N-hydroxyethyl ammonium bromide ("DMRIE"); stearylamine; dimethyldioctadecylammonium bromide; and 3B—[N',N'-dimethylaminoethane)-carbamol. In another embodiment, the cationic lipid is, for example, stearylamine, DC-Cholesterol, dimethyldioctadecylammonium bromide, or 3B—[N',N'-dimethylaminoethane)-ca-rbamol. Suitable mucoadhesive compounds include, but are not limited to, Carbopol 934 P, polyaxomers, carbomers and plant lectins.

In one embodiment, the aqueous phase includes, but is not limited to, sterile water sterile saline and sterile, isotonic aqueous solutions buffered in the pH range of about 6.5 to about 8.5 with, for example, sodium acetate, sodium phosphate, boric acid and the like. Other suitable pharmaceutical carriers are described in Remington's Pharmaceutical Sciences. In another embodiment, the therapeutic agent is present in the aqueous phase.

In one embodiment, the lipid formulation further comprises a preservative, such as an antioxidant. Suitable preservatives/antioxidants include, but are not limited to, tocoperol (e.g., alpha-tocopherol), tocopherol derivatives, butylated hydroxyanisole and butylated hydroxytoluene.

In another embodiment, the lipid formulation further comprises a modifying agent including, but not limited to, cholesterol, stearylamine, cholesteryl hemisuccinate, phosphatidic acids, dicetyl phosphate and fatty acids. In still another embodiment, the lipid formulation further comprises a wetting agent. Suitable wetting agents include, but are not limited to, polyoxyethylene, sorbitan monolaurate and stearate. In still another embodiment, the lipid formulation further comprises a thickening agent. Suitable thickening agents include, but are not limited to, hydroxyethylcellulose, hydroxypropylmethylcellulose, methylcellulose, polyvinyl alcohol and polyvinylpyrrolidone. In another embodiment, the lipid formulation further comprises a preservative (e.g., antioxidant), a modifying agent, a wetting agent, a thickening agent or a combination of any or all of the foregoing.

The following Example is presented to demonstrate certain aspects of the present invention. As such, it is to be treated as exemplary of the present invention and not to be treated as being limiting thereof.

EXAMPLES

Materials and Methods

Bacteria

*Staphylococcus aureus* strain 8325-4 is a well-characterized laboratory strain that has been used in numerous studies of experimental keratitis in both rabbit and murine models. All *S. aureus* isolates (Table 1) were grown at 37° C. on tryptic soy agar (TSA, Becton Dickinson and Co., Sparks, Md.) and sub-cultured in tryptic soy broth (TSB, Becton Dickinson and Co.) at 37° C. for 18 hours.

Animals

New Zealand White rabbits (n≥4 eyes per group) were obtained from Harlan Sprague Dawley, Inc. (Indianapolis, Ind.). All animals were specific-pathogen free and were maintained according to institutional guidelines and tenets of the ARVO Statement for the Use of Animals in Ophthalmic and Vision Research.

Before any procedure was performed, each rabbit was anesthetized.

Hemolysis Assays

Freshly collected rabbit erythrocytes were centrifuged to a pellet and resuspended in 10 mM phosphate-buffered saline (PBS; pH 7.2) with 0.02% gelatin; this washing procedure was repeated three times. Washed erythrocytes were diluted to a concentration of $10^8$ cells per mL. Purified α-toxin in (Sigma-Aldrich, St. Louis, Mo.) was serially diluted twofold in microtiter plates, rabbit erythrocytes ($10^7$ per well) were added to the α-toxin dilutions, and the plates were incubated at 37° C. until the erythrocytes in the control lacking α-toxin had settled. The highest dilution producing red cell lysis was considered the end point. One hemolytic unit was equivalent to an α-toxin dilution that lysed erythrocytes but could not cause lysis on further dilution.

For inhibition of hemolysis, supernatants of overnight cultures or purified α-toxin samples were serially diluted twofold in a fashion similar to that described above for assays performed using α-toxin. Erythrocytes ($10^7$ per well) were mixed at 4° C. with PBS, 0.1% CD (Sigma), or 0.1% CD-cholesterol (Sigma) and then added to dilution of the culture supernatant or purified toxin in microtiter plates. The dilutions producing lysis were observed after 30 minutes. All hemolipis inhibition assays were performed in duplicate or triplicate and were repeated twice.

Intrastromal Injection of α-Toxin

α-Toxin (12 hemolytic units) was injected into the stroma of rabbit corneas (n≥4 eyes) to evaluate the subsequent development of pathologic changes at 7 hours after toxin injection.

α-Toxin in PBS or α-toxin in 1% CD, or 1% CD-cholesterol was incubated for 30 minutes at 4° C. then injected into rabbit corneas (n≥4 per group) pathologic changes were observed and the diameter of erosions was measured at 2, 5, and 7 hours postinjection using fluorescein strips (Fluorets, Aubenas, France). By 7 hours after injection, the epithelial erosions in eyes injected with c,-toxin in PBS reached their maximal diameter. Heat-inactivated α-toxin (n=4 eyes) served as a negative control.

TABLE 1

In Vitro Analysis of CD-Cholesterol Inhibition of Alpha-Toxin Activity

| Strain | Alpha-Toxin Titer | CD-Cholesterol Titer* | Fold Reduction |
|---|---|---|---|
| 8325-4 | 2048 | 0 | 2048 |
| 70490 | 32 | 8 | 4 |
| 60171 | 128 | 4 | 32 |
| 30084 | 16 | 0 | 16 |
| 30281 | 64 | 16 | 4 |
| 30155 | 128 | 16 | 8 |

Residual hemolysis can, to a limited degree, be mediated by a hemolysin other than alpha-toxin (e.g., gamma-toxin).

Experimental Keratitis

Rabbits (n≥4 eyes per group) were infected as previously described, injecting approximately 100 colony forming units (CFU) of strain 8325-4 or strain 60171, a clinical isolate, in 10 μL of TSB into the stroma of the cornea. Accuracy of the inoculum size was verified by plating aliquots (100 μL) of serial dilutions in triplicate on TSA.

Treatment of Keratitis

At 7 hours postinfection (PI), treatment began and consisted of a single topical drop of PBS, 1% CD, or 1% CD-cholesterol every 15 minutes from 7 to 8 hours PI. Then, beginning at 8.5 hours PI, a single drop was administered every 30 minutes until 13 hours PI; a total of 15 drops per eye. At 13 hours PI, corneal erosions were measured and all eyes underwent slit lamp examination (SLE) to quantify pathologic changes.

Slit Lamp Examination

SLE of pathologic changes of rabbit eyes was performed by two masked observers as described previously.

Colony Forming Unit Determination

Corneas of rabbits infected with either *S. aureus* 8325-4 or 60171 were harvested at 14 hours PI and bacteria were quantified as described previously.

Statistics

Statistical analyses were performed using statistical analysis software (SAS [Cary, N.C.] or Microsoft Excel [Seattle, Wash.]) as previously described.

Results

In Vitro Inhibition of α-Toxin

Figure 1:
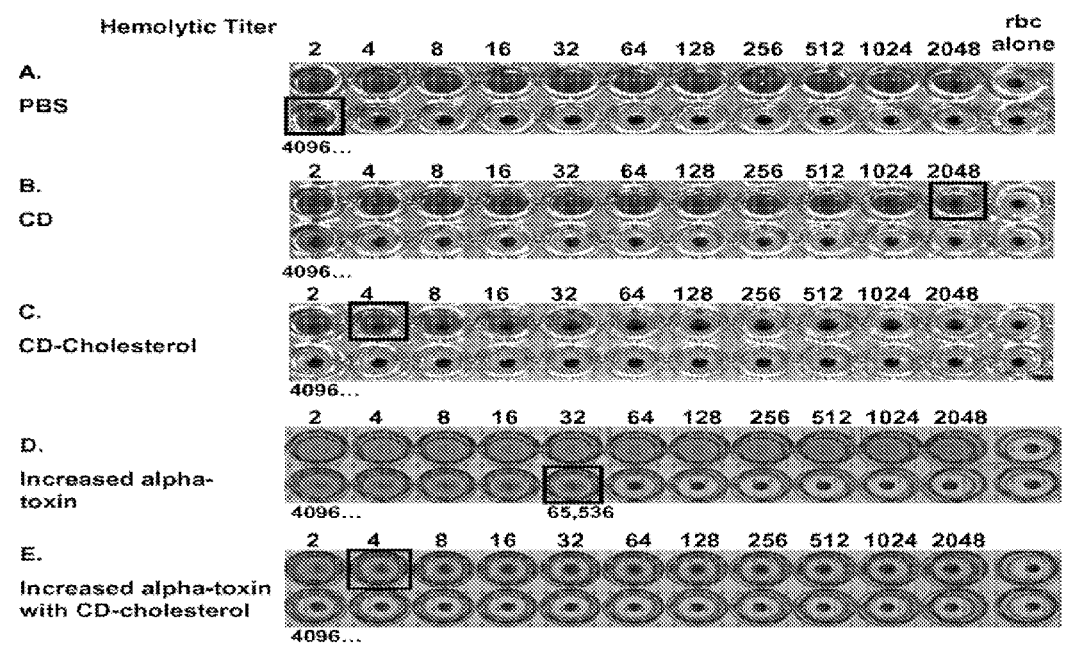

To test whether CD or CD-cholesterol could inhibit the action of α-toxin, aliquots of erythrocytes were mixed with PBS, 0.1% CD, or 0.1% CD-cholesterol and then added to serial dilutions of purified α-toxin. The α-toxin titer for the sample in PBS was approximately 4096 (FIG. 1A). The α-toxin titer for the mixture with CD was reduced only twofold compared with the mixture with only PBS (FIG. 1B). In contrast, the hemolysis titer of the same amount of α-toxin incubated with CD-cholesterol was approximately 4 (FIG. 1C), a reduction in titer of 500-fold.

A higher concentration of α-toxin was tested for inhibition using 0.1% CD-cholesterol. The hemolytic titer of the α-toxin in PBS was 65,536 (FIG. 1D), but when the α-toxin preparation was incubated with CD-cholesterol the titer was reduced to 4, approximately a 16,000-fold decrease in hemolytic activity.

The ability of CD-cholesterol to inhibit the hemolytic activity of α-toxin in culture supernatants of multiple *S. aureus* strains was then tested. Rabbit erythrocytes incubated with CD-cholesterol or PBS were added to serially diluted culture supernatants of six *S. aureus* strains. For all six strains tested, at least a fourfold inhibition of hemolytic activity was observed (Table 1).

In Vivo Inhibition of α-Toxin

Because CD-cholesterol inhibits hemolysis of rabbit erythrocytes by α-toxin, there was interest in determining if this inhibitor could limit α-toxin effects on the rabbit cornea. α-toxin (12 hemolytic units) was incubated with PBS, 1% CD, or 1% CD-cholesterol for 30 minutes at 4° C. After incubation, each mixture was injected intrastromally into rabbit corneas and the size of epithelial erosion was measured at 2, 5, and 7 hours, the latter being the time of maximal erosion diameter (FIG. 2).

The corneal erosion sizes at all times studied for the eyes receiving toxin mixed with CD-cholesterol were significantly smaller than that of eyes receiving toxin mixed with PBS (P≤0.0165; Table 2).

TABLE 2

Erosion Diameters of Rabbit Injected with Alpha-Toxin Mixed with 1% CD-Cholesterol, 1% CD, or PBS

| Time Postinjection | Erosion Diameter (mm ± SEM) | | | P-value | | |
|---|---|---|---|---|---|---|
| | CD-Cholesterol | CD | PBS | CD-Cholesterol vs. CD | CD-Cholesterol vs. PBS | CD vs. PBS |
| 2 hours | 1.75 ± 1.03 | 2.40 ± 1.22 | 6.20 ± 0.35 | 0.6925 | 0.0165 | 0.0131 |
| 5 hours | 3.00 ± 0.71 | 5.30 ± 1.15 | 7.05 ± 0.50 | 0.1173 | 0.0028 | 0.1977 |
| 7 hours | 3.88 ± 0.66 | 8.10 ± 0.23 | 7.64 ± 0.33 | 0.0048 | 0.0041 | 0.2984 |

The erosion sizes of eyes injected with toxin mixed with CD alone were significantly smaller than that of eyes injected with toxin mixed with PBS at 2 hours postinjection (P=0.0131), but not at 5 or 7 hours postinjection (P≥0.1977).

The corneal erosion sizes of eyes injected with toxin mixed with CD-cholesterol were significantly smaller than that of eyes injected with toxin mixed with CD alone at 7 hours postinjection (P=0.0048), but not at 2 or 5 hours postinjection (P≥0.1173).

In Vivo Treatment of *S. aureus* Keratitis

The studies described above demonstrate that the lytic effects of α-toxin on erythrocytes and the effects of purified toxin on rabbit corneas can be inhibited by CD-choleterol. These finding raised the possibility that CD-cholesterol could treat corneas infected with *S. aureus*. Rabbit corneas were injected with either *S. aureus* strain 8325-4 or *S. aureus* clinical isolate 60171. Rabbit eyes were treated from 7 to 13 hours PI with PBS, 1% CD, or 1% CD-cholesterol. At 13 hours PI, the rabbits were observed for pathological changes, and erosion formation (FIG. 2B). At 14 hours PI, the rabbits were euthanatized and the corneal tissue was harvested to determine the number of bacteria present.

At 13 hours PI, *S. aureus* strain 8325-4 infected eyes were evaluated by SLE to quantify pathologic changes. Eyes treated with PBS had an average SLE score of 9.94±0.37 (FIG. 3A). The eyes treated with CD had an average SLE score of 9.23±0.39, which was statistically similar to the PBS treated eyes (P=0.4002). In contrast, eyes treated with CD-cholesterol had a significantly lower SLE score of 6.35±0.28 (P=0.0017). The SLE score of the rabbits treated with CD-cholesterol was significantly lower than the SLE score of the eyes treated with CD (P=0.0103).

At 13 hours PI, eyes infected with *S. aureus* strain 8325-4 and treated with PBS developed erosions of 5.89±0.36 mm in diameter (FIG. 3B). Eyes treated with CD had corneal erosions of 4.55±0.28 mm, a size significantly smaller than that of eyes treated with PBS (P=0.0103). Eyes treated with CD-cholesterol had corneal erosions measuring 4.25±0.20 mm in diameter, a size also significantly smaller than the PBS-treated eyes (5.89±0.36; P=0.0017). The eyes treated with CD-cholesterol or CD had similar erosion sizes (P=0.4002).

The number of surviving *S. aureus* 8325-4 was determined at 14 hours PI. The PBS treated eyes had $1.12 \times 10^7 \pm 3.66 \times 10^6$ bacteria per cornea. The eyes treated with CD-cholesterol or CD had $5.04 \times 10^6 \pm 1.56 \times 10^6$ or $9.36 \times 10^6 \pm 4.22 \times 10^5$ bacteria per cornea, respectively, which was not significantly different from the number of bacteria per cornea in the eyes treated with PBS (P≥0.1941). The eyes treated with CD-cholesterol and CD had statistically similar numbers of bacteria (P=0.0648).

Strain 60171, an ocular clinical isolate, was injected into the corneas of rabbits to determine the effectiveness of treatments with CD-cholesterol, CD, or PBS. As described above, the pathologic changes and erosion development were observed via SLE at 13 hours PI (FIG. 2B) whereas the number of surviving bacteria was determined at 14 hours PI.

Eyes treated with PBS had an average SLE score of 9.38±0.53 (FIG. 4A). The eyes treated with CD had an average SLE score of 9.02±0.90, a score which was statistically the eyes treated with PBS (P=0.7403). In contrast, eyes treated with CD-cholesterol had reduced pathology compared with PBS treated eyes; the average SLE score of CD cholesterol treated eyes was 4.83±0.30, a value which was significantly lower than the eyes treated with PBS (P<0.0001). Furthermore, the eyes treated with CD-cholesterol had statistically lower average SLE scores than the eyes treated with CD (P=0.0013).

The diameter of corneal epithelial erosions of eyes infected with 60171 and treated with PBS was 5.33±0.21 mm (FIG. 4B). The diameter of corneal erosions in eyes treated with CD was 4.83±0.31 mm, a size statistically similar to eyes treated with PBS (P=0.2131). In contrast, eyes treated with CD-cholesterol had significantly smaller corneal erosions measuring 3.83±0.17 mm than either the PBS-treated or CD-treated eyes (P=0.0003 or P=0.0220, respectively).

At 14 hours PI, the corneas were harvested to obtain the log number of CFU present in the corneas. There were 1.48×

$10^7 \pm 2.55 \times 10^6$ bacteria in the corneas of the eyes treated with PBS. In the eyes treated with CD, there were $2.42 \times 10^7 \pm 8.96 \times 10^6$ bacteria, which is not significantly different from the eyes treated with PBS (P=0.4687). There were $8.78 \times 10^6 \pm 1.61 \times 10^6$ bacteria found in eyes treated with CD-cholesterol which was similar to the numbers of bacteria found in the eyes treated with CD or with PBS (P±0.1017).

Throughout this application, and specifically in the list below, various references are cited. All such references are incorporated herein by reference in their entirety.

REFERENCES

Shetty A K, Kumar A. Osteomyelitis in adolescents. *Adolesc Med State Art Rev.* 2007; 18(1):79-94.

Popovich K J, Hota B, Weinstein R A. Treatment of community-associated methicillin-resistant *Staphylococcus aureus*. *Curr Infect Dis Rep.* 2008; 10(5):411-420.

Fowler V G Jr, Miro J M, Hoen B, et al. *Staphylococcus aureus* endocarditis: a consequence of medical progress. *JAMA.* 2005; 293(24):3012-3021.

Kielian T, Syed M M, Liu S, et al. The synthetic peroxisome proliferators-activated receptor gamma agonist ciglitazone attenuates neuroinflammation and accelerates encapsulation in bacterial brain abscesses. *J Immunol.* 2008; 180(7): 5004-5016.

Kuehnert M J, Hill H A, Kupronis B A, Tokars J I, Solomon S L, Jernigan D B. Methicillin-resistant-*Staphylococcus aureus* hospitalizations, United States. Emerg Infect Dis. 2005; 11(6):868-872.

Klevens R M, Morrison M A, Nadle J, et al. Invasive methicillin-resistant *Staphylococcus aureus* infections in the United States. *JAMA.* 2007; 298(15):1763-1771.

Kuehnert M J, Kruszon-Moran D, Hill H A, et al. Prevalence of *Staphylococcus aureus* nasal colonization in the United States. 2001-2002. *J Infect Dis.* 2006; 193(2):172-179.

Klevens R M, Edwards J R, Tenover F C, et al. Changes in the epidemiology of methicillin-resistant *Staphylococcus aureus* in intensive care units in US hospitals, 1992-2003. *Clin Infect Dis.* 2006; 42(3):389-391.

Moran G J, Krishnadasan A, Gorwitz R J, et al. Methicillin-resistant *S. aureus* infections among patients in the emergency department. *N Engl J Med.* 2006; 355(7):666-674.

Liesegang T J. The Cornea. Boston, Mass.: Butterworth-Heineman; 1998:159-219.

Kattan H M, Flynn H W Jr, Pflugfelder S C, Robertson C, Forster R K. Nosocomial endophthalmitis survey. Current incidence of infection after intraocular surgery. *Ophthalmology.* 1991; 98(2):227-238.

McCulley J P, Shine W E. Changing concepts in the diagnosis and management of blepharitis. *Cornea.* 2000; 19(5):650-658.

O'Callaghan R J. Role of exoproteins in bacterial keratitis: the Fourth Annual Thygeson Lecture, presented at the Ocular Microbiology and Immunology Group Meeting, Nov. 7, 1998. *Cornea.* 1999; 18(5):532-537.

Callegan M C, Engel L S, Hill J M, O'Callaglan R J. Corneal virulence of *Staphylococcus aureus*: roles of alpha-toxin and protein A in pathogenesis. *Infect Immun.* 1994; 62(6): 2478-2482.

O'Callaghan R J, Callegan M C, Moreau J M, et al. Specific roles of alpha-toxin during *Staphylococcus aureus* corneal infection. *Infect Immun.* 1997; 65(5):1571-1578.

Moreau J M, Sloop G D, Engel L S, Hill J M, O'Callaghan R J. Histopathological studies of staphylococcal alpha-toxin: effects on rabbit corneas. *Curr Eye Res.* 1997; 16(12): 1221-1228.

Kielian T, Cheung A, Hickey W F. Diminished virulence of an alpha-toxin mutant of *Staphylococcus aureus* in experimental brain abscesses. *Inject Immun.* 2001; 69(11):6902-6911.

DeLeo F R, Otto M. An antidote for *Staphylococcus aureus* pneumonia? *J Exp Med.* 2008; 205(2):271-274.

Phillips J R, Tripp T J, Regelmann W E, Schlievert P M, Wangensteen O D. Staphylococcal alpha-toxin causes increased tracheal epithelial permeability. *Pediatr Pulmonol.* 2006; 41(12):1146-1152.

Bubeck Wardenburg J, Schneewind O. Vaccine protection against *Staphylococcus aureus* pneumonia. *J Exp Med.* 2008; 205(2):287-294.

Valeva A, Weisser A, Walker B, et al. Molecular architecture of a toxin pore: a 15 residue sequence lines the transmembrane channel of staphylococcal α-toxin. *EMBO J* 1996; 15(8): 1857-1864.

Liang X, Ji Y. Involvement of a5β1-integrin and TNF-α: in *Staphylococcus aureus* alpha-toxin-induced death of epithelial cells. *Cell Microhiol.* 2007; 9(7):1809-1821.

Hasliner B, Strangfeld K, Peters G, Schulze-Osthoff K, Sinha B. *Staphylococcus aureus* alpha-toxin induces apoptosis in peripheral blood mononuclear cells: role of endogenous tumor necrosis factor-alpha and the mitochondrial death pathway. *Cell Microhiol.* 2003; 5(10):729-741.

Haslinger-Löffler B, Kahl B C, Grundmeier M, et al. Multiple virulence factors are required for *Staphylococcus aureus*-induced apoptosis in endothelial cells. *Cell Microbiol* 2005; 7(8):1087-1097.

Haslinger-Löffler B, Wagner B, Brück M, et al. *Staphylococcus aureus* induces caspase-independent cell death in human perito-neal mesothelial cells. *Kidney Int.* 2006; 70(6):1089-1098.

Eichstaedt S, Gäbler K, Below S, et al. Effects of *Staphylococcus aureus*-hemolysin A on calcium signaling in immortalized human airway epithelial cells. Cell Calcium. 2008; doi:10.1016/j.ceca.2008.09.001 [Epub ahead of print].

Johansson D, Johansson A, Behnam-Motlagh P. Alpha-toxin of *Staphylococcus aureus* overcomes acquired cisplatin-resistance in malignant mesothelioma cells. *Cancer Lett.* 2008; 265(1):67-75.

Girgis D O, Sloop G D, Reed J M, et al. A new topical model of *Staphylococcus* corneal infection in the mouse. *Invest Ophthalmol Vis Sci.* 2003; 44(4):1591-1597.

Girgis D O, Sloop G D, Reed J M, O'Callaghan R J. Effects of toxin production in a murine model of *Staphylococcus aureus* keratitis. *Invest Ophthalmol Vis Sci.* 2005; 46(6): 2064-2070.

Yotis W W, Savoy Z T. Reduction of the cytolytic action of staphylococcal alpha-toxin by progesterone. *Yale J Biol Med.* 1970; 42(6):411-419.

Raff M J, Barnwell P, Werner A S. Detoxification of staphylococcal alpha-toxin by hydrocortisone and methylprednisolone. J Med Microbiol. 1978; 11(1):67-73.

Pany S, Vijayvargia R, Krishnasastry M V. Caveolin-1 binding motif of alpha-hemolysin: its role in stability and pore formation. *Biochem Biophys Res Commun.* 2004; 322(1): 29-36.

Vijayvargia R, Kaur S, Sangha N, et al. Assembly of alpha-hemolysin on A431 cells leads to clustering of Caveolin-1. *Biochem Biophys Res Commun.* 2004; 324(3):1124-1129.

Gu L Q, Bayley H. Interaction of the non-covalent molecular adapter, beta-cyclodextrin, with the staphylococcal alpha-hemolysin pore. *Biophys J* 2000; 79(4):1967-1975.

Vijayvargia R, Suresh C G, Krishnasastry M V. Functional form of Caveolin-1 is necessary for the assembly of alpha-hemolysin. *Biochem Biophys Res Commun.* 2004; 324(3): 1130-1136.

Karginov V A, Nestorovich E M, Schmidtmann F, et al. Inhibition of *S. aureus* alpha-hemolysin and *B. anthracis* lethal toxin by beta-cyclodextrin derivatives. *Bioorg Med Chem.* 2007; 15(16): 5424-5431.

Dajcs J J, Austin M S, Sloop G D, et al. Corneal pathogenesis of *Staphylococcus aureus* strain Newman. *Invest Ophthalmol Vis Sci.* 2002; 43(4):1109-1115.

Dajcs J J, Thibodeaux B A, Girgis D O, O'Callaghan R J. Corneal virulence of *Staphylococcus aureus* in an experimental model of keratitis. *DNA Cell Biol.* 2002; 21(5-6): 375-382.

39. Hume E B, Dajcs J J, Moreau J M, O'Callaghan R J. Immunization with alpha-toxin toxoid protects the cornea against tissue damage during experimental *Staphylococcus aureus* keratitis. *Infect Immun.* 2000; 68(10):6052-6055.

Matthews L, Berry A, Ohanian V, et al. Caveolin mediates rapid glucocorticoid effects and couples glucocorticoid action to the antiproliferative program. *Mol Endocrinol.* 2008; 22(6):1320-1330.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the Specification, including the Figures and Attachment 1 be considered as exemplary only, and not intended to limit the scope and spirit of the invention.

Unless otherwise indicated, all numbers expressing quantities of ingredients, properties such as reaction conditions, and so forth used in this disclosure, including the Drawings and Attachment A are to be understood as being modified in all instances by the term "about." Accordingly, unless indicated to the contrary, the numerical parameters set forth herein are approximations that may vary depending upon the desired properties sought to be determined by the present invention.

Notwithstanding that the numerical ranges and parameters setting forth the broad scope of the invention are approximations, the numerical values set forth in the experimental or example sections are reported as precisely as possible. Any numerical value, however, inherently contain certain errors necessarily resulting from the standard deviation found in their respective testing measurements. Additionally, the invention is also not limited to human use, and encompasses the use of ocular solutions for veterinary use.

We claim:

1. A method for inhibiting damage to a mammalian cornea during *staphylococcus aureus* keratitis, comprising administering an effective *staphylococcus aureus* α-toxin inhibiting amount of a composition that comprises a β-cyclodextrin and cholesterol.

2. The method of claim 1, wherein the composition further comprises a pharmaceutically acceptable carrier.

3. The method of claim 1, wherein the β-cyclodextrin is a methylated-β-cyclodextrin.

4. The method of claim 1, wherein the composition comprises about 0.1 to about 5% cholesterol.

5. The method of claim 1, wherein the composition comprises about 0.1% to about 5% β-cyclodextrin.

6. The method of claim 1, further comprising a therapeutically effective amount of a steroid or an antibiotic.

* * * * *